(12) United States Patent
Ladisch et al.

(10) Patent No.: US 10,072,253 B2
(45) Date of Patent: Sep. 11, 2018

(54) LIQUEFIED CELLULOSIC BIOMASS FOR ENZYME PRODUCTION

(71) Applicant: PURDUE RESEARCH FOUNDATION, West Lafayette, IN (US)

(72) Inventors: Michael Ralph Ladisch, West Lafayette, IN (US); Eduardo de Aquino Ximenes, West Lafayette, IN (US); Thomas Richard Kreke, West Lafayette, IN (US); Alberto Colli Badino, Jr., Sao Carlos (BR); Fernanda Marisa da Cunha, Sao Carlos (BR); Cristiane Sanchez Farinas, Sao Carlos (BR)

(73) Assignees: Purdue Research Foundation, West Lafayette, IL (US); Federal University of Sao Carlos, Sao Carlos (BR); Brazilian Agricultural Research Corporatio—Embrapa, Sao Carlos (BR)

( * ) Notice: Subject to any disclaimer, the term of this patent is extended or adjusted under 35 U.S.C. 154(b) by 216 days.

(21) Appl. No.: 14/849,276

(22) Filed: Sep. 9, 2015

(65) Prior Publication Data

US 2016/0068828 A1 Mar. 10, 2016

Related U.S. Application Data

(60) Provisional application No. 62/048,159, filed on Sep. 9, 2014.

(51) Int. Cl.
*C12N 9/42* (2006.01)
*C12N 1/22* (2006.01)
*C12N 1/14* (2006.01)
*C12N 1/20* (2006.01)
*C12P 21/02* (2006.01)

(52) U.S. Cl.
CPC ............ *C12N 9/2437* (2013.01); *C12N 1/14* (2013.01); *C12N 1/20* (2013.01); *C12N 1/22* (2013.01); *C12P 21/02* (2013.01); *C12P 2201/00* (2013.01); *C12Y 302/01004* (2013.01)

(58) Field of Classification Search
None
See application file for complete search history.

(56) References Cited

PUBLICATIONS

De Souza et al., Biotechnology for Biofuels, 2011, 4:40, p. 1-16, http://www.biotechnologyforbiofuels.com/content/4/1/40.*
Dekker et al., Biotechnology and Bioengineering, 1983, vol. XXV, p. 3027-3048.*
Cunha et al., Bioresource Technology, 2012, vol. 112, p. 270-274.*
Harrison et al., Bioresource Technology, 2013, vol. 148, p. 105-113, available online Aug. 2013, 27 pages PDF.*
J. Sendelius (Master of Science Thesis, 2005, Lund Institute of Technology, Dept. of Chemical Engineering, Lund University, Sweden, 8 pages.*
Barrios-Gonzalez, J., Solid-state fermentation: Physiology of solid medium, its molecular basis and applications. Process Biochemistry 47 (2012) 175-185.
Pereira, L., et al., Sugarcane bagasse enzymatic hydrolysis: rheological data as criteria for impeller selection. J Ind Microbial Biotechnol (2011) 38:901-907.
Pinto, G., et al., Selection of Tannase-Producing Aspergillus Niger Strains. Brazilian Journal of Microbiology (2001) 32:24-26.
Cunha, F.M., et al., Sequential solid-state and submerged cultivation of Aspergillus niger on sugarcane bagasse for the production of cellulase. Bioresource Technology 112 (2012) 270-274.
Delabona, P., et al., Using Amazon forest fungi and agricultural residues as a strategy to produce cellulalytic enzymes. Biomass and Bioenergy, 37 (2012) 243-250.
Du, J., et al., Enzymatic liquefaction and saccharification of pretreated corn stover at high-solids concentrations in a horizontal rotating bioreactor. Bioprocess Biosyst Eng (2014) 37:173-181.
Esperanca, M.N., et al., Gas hold-up and oxygen mass transfer in three pneumatic bioreactors operating with sugarcane bagasse suspensions. Bioprocess Biosyst Eng (2014) 37:805-812.
Geddes, C.C., et al., Seed train development for the fermentation of bagasse from sweet sorghum and sugarcane using a simplified fermentation process. Bioresource Technology 128 (2013) 716-724.
Ghose, T.K., Measurement of Cellulase Activities. Pure & Appl. Chem., vol. 59, No. 2, pp. 257-268, 1987.
Jorgensen, H. et al., Liquefaction of Lignocellulose at High-Solids Concentrations. Biotechnol. Bioeng. 2007; 96: 862-870.
Kim, Y., et al., Severity Factor Coefficients for Subcritical Liquid Hot Water Pretreatment of Hardwood Chips. Biotechnol. Bioeng. 2014;111: 254-263.
Kim, Y. et al., Fractionation of cellulase and fermentation inhibitors from steam pretreated mixed hardwood. Bioresource Technology 135 (2013) 30-38.
Rodriguez-Zuniga, U. F., et al., Use of Spectroscopic and Imaging Techniques to Evaluate Pretreated Sugarcane Bagasse as a Substrate for Cellulase Production Under Solid-State Fermentation. Appl Biochem Biotechnol (2014) 172:2348-2362.
Rosgaard, L., et al., Effects of Substrate Loading on Enzymatic Hydrolysis and Viscosity of Pretreated Barley Straw. Appl. Biochem. Biotechnol. (2007) 143:27-40.
Ximenes, E., et al., Deactivation of cellulases by phenols. Enzyme and Microbial Technology 48 (2011) 54-60.
Ximenes, E., et al., Inhibition of cellulases by phenols. Enzyme and Microbial Technology 46 (2010) 170-176.

(Continued)

*Primary Examiner* — Kade Ariani
(74) *Attorney, Agent, or Firm* — Purdue Research Foundation; Zhigang Rao

(57) ABSTRACT

Methods for enhancing production of a cellulose component are disclosed herein.

2 Claims, 2 Drawing Sheets

(56) References Cited

PUBLICATIONS

Sluiter, A., et al., Determination of Structural Carbohydrates and Lignin in Biomass—Laboratory Analytical Procedure (LAP). Technical Report NREL/TP-510-42618, Revised Jul. 2011.
Stickel, J.J., et al., Rheology measurements of a biomass slurry: an inter-laboratory study. Rheol Acta (2009) 48:1005-1015.

* cited by examiner

LIQUEFIED CELLULOSIC BIOMASS FOR ENZYME PRODUCTION

CROSS-REFERENCE TO RELATED APPLICATIONS

The present U.S. patent application is related to and claims the priority benefit of U.S. Provisional Patent Application Ser. No. 62/048,159, filed Sep. 9, 2014, the contents of which is hereby incorporated by reference in its entirety into this disclosure.

BACKGROUND

This section introduces aspects that may help facilitate a better understanding of the disclosure. Accordingly, these statements are to be read in this light and are not to be understood as admissions about what is or is not prior art.

The industrial competitiveness of the 2G (cellulose) ethanol depends on achieving efficient production and use of cellulase enzymes. Cellulase production by filamentous fungi may be achieved through either solid-state fermentation (SSF) or submerged fermentation (SmF). Despite many advantages of SSF over SmF, enzyme production in large-scale SSF bioreactors is hindered by low solids loadings, or if high solids are used, by solids handling and mass and heat transfer gradients during the cultivation process (Barrios-Gonzalez, 2012; Cunha et al., 2012; Esperança et al., 2014). Submerged cultivations with high solids loadings remain challenging since mass transfer and gas hold-up limitations are also compounded by viscosity increases that occur during the first hours of cultivation as a result of fungal growth. There is therefore an unmet need for enhancing production of cellulase components.

SUMMARY

In one aspect, disclosed herein is a method for enhancing production of a cellulase component. The method includes the step of fermenting a microorganism that produces a cellulolytic component in a slurry of lignocellulosic biomass. The slurry of lignocellulosic biomass can have steam exploded (pretreated) bagasse. In another aspect, the method includes the step of liquefying the bagasse prior to fermentation. The lignocellulosic biomass is selected from the group comprising at least one of steam-exploded bagasse, corn stalks, wheat straw, energy cause residue, switch grass, hard wood, and soft wood. In one aspect, the cellulase enzyme component is endoglucanase. In another aspect, the cellulase enzyme component is exoglucanase. In yet another aspect, the cellulase enzyme component is β-glucosidase. In yet another aspect, the cellulase enzyme component is the hemicellulase component xylanase. In yet another aspect, the cellulase enzyme component is β-xylosidase. In yet another aspect, the cellulase enzyme component is a lignin degrading enzyme. In yet another aspect, the cellulase enzyme component has at least one of amylase, pectinase, and protease. In yet another aspect, the microorganisms are selected from at least one of fungal microorganisms *Aspergillus oryzae, Trichoderma harzianum, Penicillium verryculosum, Humicolagrisea,* and *Phanerochaeta chrysosporium*. In another aspect, the microorganism is *Bacillus* sp. In yet another aspect, the microorganism is *Caldicellulosiraptor bescii* G1A. In yet another aspect, the microorganism is *Aspergillus niger*.

DETAILED DESCRIPTION

Figure 1:
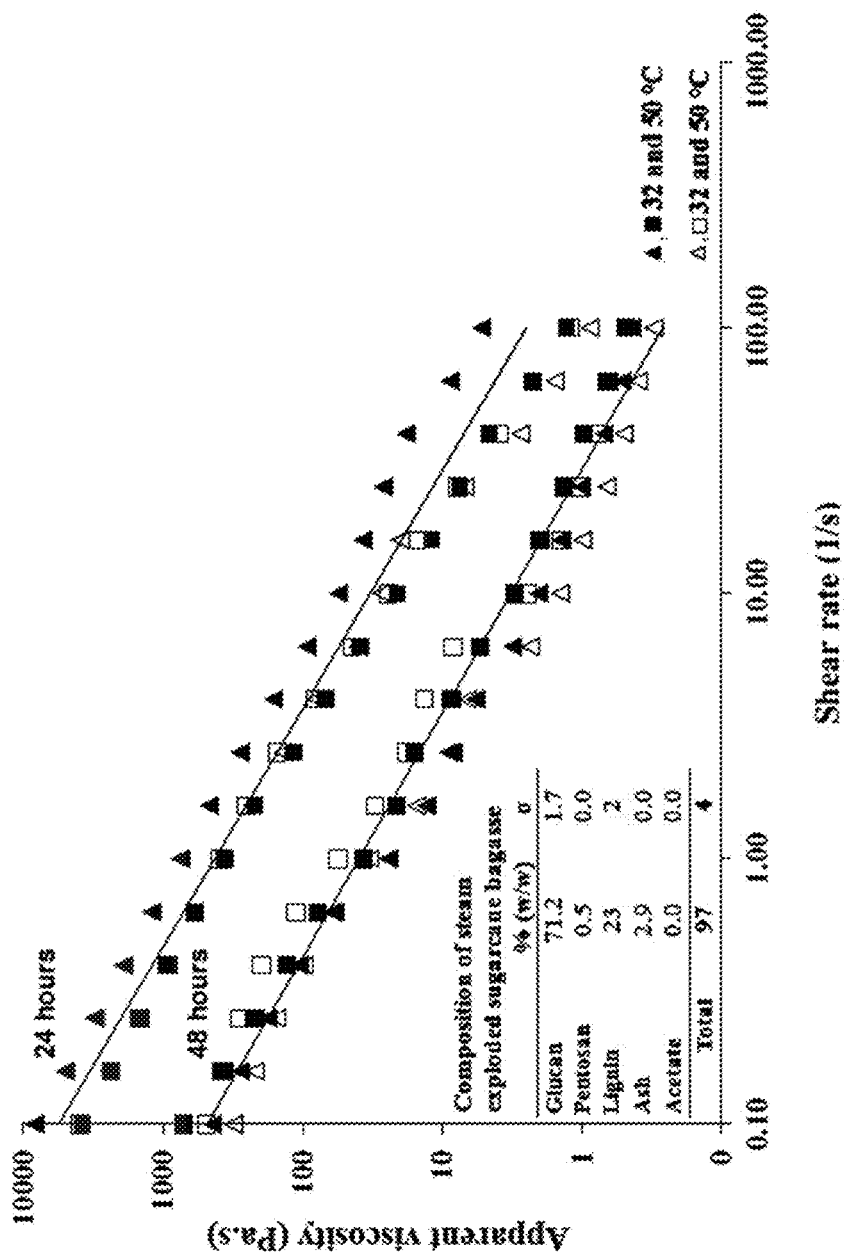
FIG. 1 shows change in viscosity as a function of shear rate after 24 and 48 hours incubation with 301 IU endoglucanase per gram of dry bagasse.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

Disclosed herein are methods for liquefaction of pretreated and sterilized sugarcane bagasse for enhancing endoglucanase production through submerged fermentation by *Aspergillus niger*. After initial solid state fermentation of steam pretreated bagasse solids by *A. niger*, fed-batch addition of the substrate to cellulase in buffer over a 12 h period, followed by 36 h reaction, resulted in a liquid slurry with a viscosity of 0.30 ±0.07 Pa·s at 30% (w/v) solids. Addition of *A. niger* for submerged fermentation of sterile liquefied bagasse at 23% w/v solids resulted in an enzyme titer of 2.5 IU. $mL_{-1}$ or about 15× higher productivity than solid-state fermentation of non-liquefied bagasse (final activity of 0.17 $IU·mL^{-1}$). Bagasse not treated by initial solid-state fermentation but liquefied with enzyme gave 2 $IU·mL^{-1}$. These results demonstrate the utility of liquefied bagasse as a culture medium for enzyme production in submerged fermentations.

Effects of the total solids loading on rheological behavior of cellulosic and lignocellulosic suspensions with the aim of improving the enzymatic hydrolysis of cellulose have been reported (Du et al., 2014; Jorgensen et al., 2007; Stickel et al., 2009. Rheological properties of sugarcane bagasse, specifically, were studied by Geddes et al. (2013) and Caldas Pereira et al. (2011), who demonstrated that a small amount of enzyme is able to decrease the viscosity of pretreated sugarcane bagasse slurries with improvements in hydrolysis coinciding with improved flow properties. Esperanca et al. (2014) described hydrodynamic effects of carrying out microbial fermentation in a pneumatic bioreactor system at solids contents between 3 and 20% w/v.

The present disclosure reports enzymatic and microbial liquefaction of steam exploded sugarcane bagasse in a fed-batch system followed by endoglucanase production at high solids loading by an *Aspergillus niger* wild type strain isolated from the Brazilian biome.

EXAMPLE

Methods
Material

The inducer substrate for endoglucanase production was steam exploded sugarcane bagasse (particle size of 1 to 2 mm) from the Sugarcane Research Center (CTC, Brazil). The steam explosion was conducted at 1667 kPa and 205° C. for 20 min. Composition of the pretreated bagasse, determined by standard NREL protocol (Sluiter et al., 2008) was 71% (w/w) glucan, 0.5% pentosan, 27.8% lignin and 3% ash. Sugarcane bagasse, before pretreatment, has a composition of 39% cellulose (glucan), 27.7 pentosans (including acetyl), 24.8% lignin, 3.9% ash, and 5.7% extractives (Ladisch et al., 2013).

Microorganism:

*Aspergillus niger* wild type A12 strain, from Embrapa Food Technology collection (Rio de Janeiro, Brazil), isolated from black pepper (Couri & deFarias, 1995) and maintained at −18° C. in a 20% (w/w) glycerol/water solution, was activated in potato dextrose agar medium slants for 4 days at 32° C. The spores were suspended by adding 0.3% Tween 80 (v/v) to the slants and their concentration was determined by counting in a Neubauer chamber.

Nutrient Medium

Mandels nutrient medium was adapted from Mandels and Sternberg (1976) according to (Cunha et al., 2012) and contained (w/v): 0.14% $(NH_4)_2SO_4$, 0.20% $KH_2PO_4$, 0.03% $CaCl_2$, 0.02% $MgSO_4 \cdot 7H_2O$, 0.50% peptone, 0.20% yeast extract, 0.03% urea, 0.10% Tween 80 and 0.10% of salt solution (5 mg/L $FeSO_4 \cdot 7H_2O$, 1.6 mg/L, $MnSO_4 \cdot H_2O$, 1.4 mg/L $ZnSO_4 \cdot 7H_2O$, and 2.0 mg/L $CoCl_2$).

Solid State Fermentation

The solid-state fermentation (SSF) cultivations were carried out for 72 hrs at static conditions and 32° C. in 250 mL Erlenmeyer flasks containing the steam exploded sugarcane bagasse to which 12 mL nutrient medium per 5 g bagasse (dry weight basis) was added. Enzymes were extracted at 35° C. by adding fermented solids at 1:10 (w/v) 50 mM sodium citrate buffer pH 4.8 and agitating at 120 rpm for 40 min. The extracts were vacuum filtered using Whatman glass microfiber filters and kept frozen at −20° C. until analysis. Runs were carried out in triplicate.

Liquefaction of Sugarcane Bagasse

Endoglucanase C, (Genencor Division of Danisco, Rochester, N.Y.), 25 mL enzyme in 70 mL buffer was loaded into a 250 mL Erlenmeyer flask that was capped with a stopper. Pretreated bagasse was added in 4 g increments (dry weight basis) at 0, 1, 2, 3, 6, and 9 hours with an additional 6 g at 12 hours until the solids concentration was 30% w/v in 100 mL of 50 mM sodium citrate buffer, pH 4.8. Agitation was at 290 rpm in a bench top mixer (IKA, Wilmington, Del.) for 24 or 48 hours at either 32 or 50° C. Bagasse treated for 12 hours in a solid state fermentation was also liquefied using the same procedure.

Submerged Fermentation with Liquefied Sugarcane Bagasse

After the liquefaction, the slurry was sterilized at 121° C. for 30 min. Modified Mandels nutrient medium was added and the fungus *A. niger* A12 was inoculated at $10^7$ spores per gram of dry biomass. Final solids concentration was 23% (w/v). The liquefied biomass was then fermented at 32° C. and 250 rpm for 72 h in an orbital shaker incubator (New Brunswick Innova 144). After fermentation, the remaining slurry was vacuum filtered using Whatman glass microfiber filters and kept frozen for analytical assays. Runs were carried out in triplicate.

Rheological Measurements

Apparent viscosity ($\mu_{app}$) of the slurries was measured at 50° C. shear rates of 0.1 to 100 $s^{-1}$ in a model AR-G2 rheometer (TA Instruments, USA) using a starch pasting impeller and cup geometry.

Analytical Assay

Endoglucanase activity was measured with 1% (w/v) carboxymethyl cellulose in 50 mM sodium citrate buffer pH 4.8 (IUPAC, Ghose, 1987). One unit of endoglucanase activity was defined as the amount of enzyme that released 1 μmol of reducing sugar per min, using the DNS method.

Results and Discussion

Liquefaction of Sugarcane Bagasse

The first liquefaction experiments used 30% solids, all added at t=0. After 24 h of reaction, the stiffness of the sugarcane bagasse slurry was still so high that the measurement of the apparent viscosity was not possible. When the pretreated and fermented solids were added in a fed batch manner, the high initial enzyme to substrate ratio during the first hours of reaction allowed greater mixing and mass transfer. Bagasse in subsequent 4 g increments was added to a liquid slurry, thereby enabling mixing and mass transfer as the solids concentration increased and enzyme/solids ratio decreased over time. This approach was analogous to that of Rosgaard et al. (2007) for rice straw.

The resulting bagasse slurries showed non-Newtonian shear-thinning behavior. This is consistent with corn stover and 10% (w/v) sugarcane bagasse slurries (Du et al., 2014; Stickel et al. 2009; Caldas Pereira et al., 2011). The reduced viscosities are believed to reflect changes in structures of long-chain molecules and rearrangement of fibrous particles (Caldas Pereira et al., 2011; Du et al. 2014).

Figure 2B:
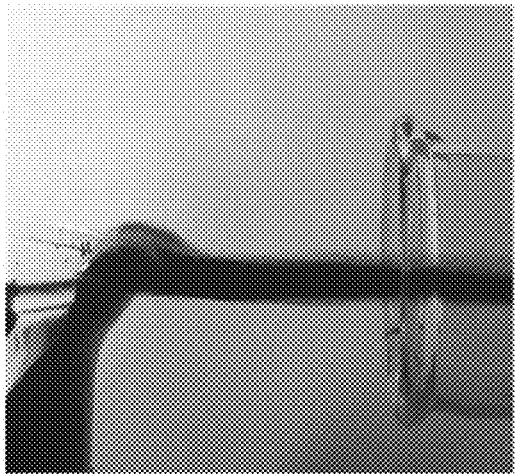
FIG. 2b is a picture of sugarcane bagasse 30% solids (w/w) after liquefaction.
Figure 2A:
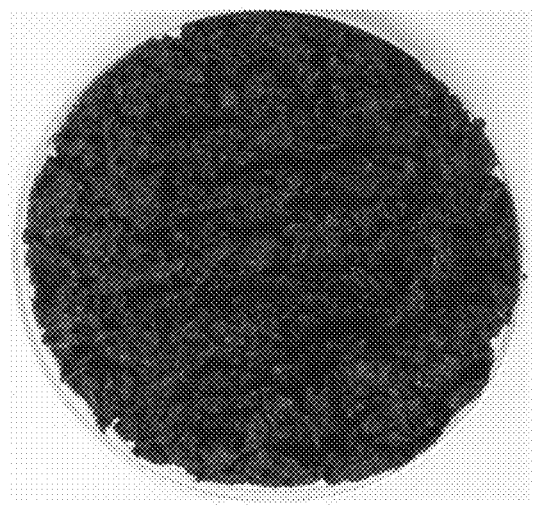
FIG. 2a is a picture of sugarcane bagasse 30% solids (w/w) before liquefaction.

Liquefaction at 50° C., which is optimal for enzyme activity, was compared to 32° C. which is suitable for *A. niger* A12 growth. The enzyme reaction results in a shear-thinning bagasse slurry (FIG. 1). Referring to FIG. 1, (▲, ■) indicate enzyme liquefaction at 32 and 50° C. or (Δ, □) enzyme combined with microbial liquefaction (Log $\mu_{app}$=c+ A·log γ. $A_{24hrs}$=−0.660, $A_{48hrs}$=−0.692); viscosity at t=0 was not measureable due to solid characteristics of bagasse at 300 g/L. Initial composition of all samples as indicated in table (analysis by NREL standard procedure (Sluiter et al., 2008). *A. niger* growth caused additional production of enzyme due to the microorganism that was carried over from the solid state fermentation. The resulting slurry had an apparent viscosity of 0.87 Pa·s at 100 $s^{-1}$ shear rate. Slopes of the data sets were similar at 24 and 48 hours for both enzyme and combined microbial and enzyme liquefaction, respectively. However, after 24 hours of reaction time, the viscosity was still too high for an efficient fermentation (upper curve in FIG. 1). A longer reaction time (48 h) decreased viscosity further (lower curve in FIG. 1). FIGS. 2*a* and 2*b* show pictures of sugarcane bagasse 30% solids (w/w) before liquefaction (FIG. 2*a*) and after liquefaction (FIG. 2*b*).

The viscosity profiles are similar at both 32 and 50° C., although enzyme stability is 4× higher at 32° C. than at 50° C. Overall, the preferred conditions are a total liquefaction time of 48 h at 32° C. for bagasse that is treated through a combination of 12 hr solid state fermentation and 36 hr enzyme assisted liquefaction. The final apparent viscosity is 0.30 Pa·s at 100 $s^{-1}$ shear rate (FIG. 1). Liquefaction using bagasse treated with enzyme, only, corresponded to 0.48 Pa·s at 100 $s^{-1}$ shear rate.

Endoglucanase Production using Liquefied Sugarcane Bagasse

Endoglucanase production by submerged fermentation at 32° C. for 72 h using sugarcane bagasse, liquefied either in the absence or presence of *A. Niger* A12 corresponded to 2 to 2.5 IU·$mL^{-1}$. Fermentation after liquefaction of this material resulted in endoglucanase activity of up to 15-fold higher than solid-state fermentation, with enzyme activities of 2.5±0.3 IU $mL^{-1}$ and 0.17±0.3 IU $mL^{-1}$ obtained in submerged and solid state cultivations, respectively.

The presence of *A. niger* A12 during liquefaction resulted in 22% higher endoglucanase titers compared to liquefaction in the absence of the fungus where endoglucanase titers were 2 IU $mL^{-1}$. In comparison, endoglucanase production on untreated bagasse obtained in this study was on the same order of that obtained by Delabona et al., 2012 after 96 h of solid-sate fermentation of untreated sugarcane bagasse by an *A. fumigatus* strain isolated from the Amazon forest. Delabona's organism gave 0.167 IU·mL$^{-1}$ endoglucanase production after 96 h of solid-state fermentation.

Liquid hot water pretreatment of sugarcane bagasse followed by additional substrate washing with distilled water gave an enzyme yield of 0.75 IU·mL$^{-1}$ which was higher than the 0.167 IU·mL$^{-1}$ for untreated substrate of Delabona (2012) (Rodriguez-Zuniga et al., 2014). Liquid hot water pretreatment cooks the lignocellulose in hot, pressurized water causing release of inhibitors into the water (Kim et al., 2013a,b). In this case, removal of microbial and enzyme inhibitors (for instance phenolic compounds) by washing may help to achieve both higher enzyme activity and enzyme production (Ximenes et al., 2010, 2011).

It is therefore demonstrated herein, for the first time, the potential application of enzyme production after liquefaction of sugarcane bagasse in order to obtain high lignocellulose concentrations. High solids loading in large-scale cultivations combine the advantages of high enzyme productivity for solid-state fermentation and the scalability of submerged fermentation.

Enzyme catalyzed liquefaction of sugarcane bagasse enables submerged fermentation of *A. niger* and production of endoglucanase at a 12-fold higher yield than solid state fermentation. When a combined enzymatic and biological liquefaction promoted by *A. niger* A12 is used, the viscosity of 0.30±0.07 Pa·s is lower than bagasse liquefied using enzyme alone (0.48±0.08 Pa·s, at 100 s$^{-1}$ shear rate). A 15-fold higher yield of endoglucanase is observed when using bagasse, processed through combined enzymatic and biological liquefaction, as culture medium in submerged fermentation.

Those skilled in the art will recognize that numerous modifications can be made to the specific implementations described above. The implementations should not be limited to the particular limitations described. Other implementations may be possible. In addition, all references cited herein are indicative of the level of skill in the art and are hereby incorporated by reference in their entirety.

1. Barrios-Gonzalez, J., 2012. Solid-state fermentation: Physiology of solid medium, its molecular basis and applications. Process. Biochem. 47, 175-185.
2. Caldas Pereira, L. T., Sobral Teixeira, R. S., da Silva Bon, E. P., Freitas, S. P., 2011. Sugarcane bagasse enzymatic hydrolysis: rheological data as criteria for impeller selection. J. Ind. Microbiol. Biotechnol. 38, 901-907.
3. Couri, S., deFarias, A. X., 1995. Genetic manipulation of *Aspergillus niger* for increased synthesis of pectinolytic enzymes. Rev. Microbiol. 26, 314-317.
4. Cunha, F. M., Esperança, M. N., Zangirolami, T. C., Badino, A. C., Farinas, C. S., 2012. Sequential solid-state and submerged cultivation of *Aspergillus niger* on sugarcane bagasse for the production of cellulase. Bioresour. Technol. 112, 270-274.
5. Delabona, P. D., Pirota, R., Codima, C. A., Tremacoldi, C. R., Rodriguez, A., Farinas, C. S., 2012. Using Amazon forest fingi and agricultural residues as a strategy to produce cellulolytic enzymes. Biomass and Bioenergy. 37, 243-250.
6. Du, J., Zhang, F., Li, Y., Zhang, H., Liang, J., Zheng, H., Huang, H., 2014. Enzymatic liquefaction and saccharification of pretreated corn stover at high-solids concentrations in a horizontal rotating bioreactor. Bioprocess. Biosyst. Eng. 37, 173-181.
7. Esperança, M. N., Cunha, F. M., Cerri, M. O., Zangirolami, T. C., Farinas, C. S., Badino, A. C., 2014. Gas hold-up and oxygen mass transfer in three pneumatic bioreactors operating with sugarcane bagasse suspensions. Bioprocess. Biosyst. Eng. 37, 805-812.
8. Geddes, C. C., Mullinnix, M. T., Nieves, I. U., Hoffman, R. W., Sagues, W. J., York, S. W., Shanmugam, K. T., Erickson, J. E., Vermerris, W. E., Ingram, L. O., 2013. Seed train development for the fermentation of bagasse from sweet sorghum and sugarcane using a simplified fermentation process. Bioresour. Technol. 128, 716-724.
9. Ghose, T. K., 1987. Measurement of cellulase activities. Pure Appl. Chem. 59, 257-268.
10. Jorgensen, H., Vibe-Pedersen, J., Larsen, J., Felby, C., 2007. Liquefaction of lignocellulose at high-solids concentrations. Biotechnol. Bioeng. 96, 862-870.
11. Kim, Y., Kreke, T., Mosier, N., and Ladisch, M., 2013a. Severity Factor Coefficients for Subcritical Liquid Hot Water Pretreatment of Hardwood Chips, Biotech. Bioeng. 111(2), 254-263 DOI: 10.1002/bit.25009.
12. Kim, Y., Kreke, T., Hendrickson, R., Parenti, J., and Ladisch, M.R., 2013b. Fractionation of Cellulase and Fermentation Inhibitors from Steam Pretreated Mixed Hardwood, Bioresour. Technol., http://dx.doi.org/10.1016/j.biortech.2012.10.130, 135, 30-38.
13. Ladisch, M. R., Ximenes, E., Kim, Y., Mosier, N. S., 2013. Biomass Chemistry, in Catalysis for the Conversion of Biomass and Its Derivatives, Behrens, M. and Dayte, A. K. (Eds.), Max Planck Research Library, Berlin, 131-164.
14. Mandels, M., Sternberg, D., 1976. Recent advances in cellulase technology. J. Ferment. Technol. 54, 267-286.
15. Rodriguez-Zuniga, U. F., Neto, V. B., Couri, S., Crestana, S., Farinas, C. S., 2014. Use of Spectroscopic and Imaging Techniques to Evaluate Pretreated Sugarcane Bagasse as a Substrate for Cellulase Production Under Solid-State Fermentation. Appl. Biochem. and Biotechnol. 172(5), 2348-2362.
16. Rosgaard, L., Andric, P., Dam-Johansen, K., Pedersen, S., Meyer, A. S., 2007. Effects of substrate loading on enzymatic hydrolysis and viscosity of pretreated barley straw. Appl. Biochem. Biotechnol. 143, 27-40.
17. Sluiter, A., Hames, B., Ruiz, R., Scarlata, C., Sluiter, J., Templeton, D., Crocker, D., 2008. Determination of ash in biomass and Determination of structural carbohydrates and lignin in biomass. Golden, Colo., USA: National Renewable Energy Laboratory.
18. Stickel, J. J., Knutsen, J. S., Liberatore, M. W., Luu, W., Bousfield, D. W., Klingenberg, D. J., Scott, C. T., Root, T. W., Ehrhardt, M. R., Monz, T. O., 2009. Rheology measurements of a biomass slurry: an inter-laboratory study. Rheol. Acta. 48, 1005-1015.
19. Ximenes, E., Kim, Y., Mosier, N., Dien, B., and Ladisch, M., 2011. Deactivation of Cellulases by Phenols. Enzyme and Microbial Technology, 48, 54-60.
20. Ximenes, E., Kim, Y., Mosier, N., Dien, B., and Ladisch, M., 2010. Inhibition of Cellulases by Phenols. Enzyme and Microbial Technology, 46, 170-176.

The invention claimed is:

1. A method of fermenting a liquefied lignocellulosic biomass for enhanced production of endoglucanase enzyme, the method comprising fermenting a lignocellulosic biomass comprising steam exploded (pretreated) bagasse in the presence of a microorganism to produce a first endoglucanase enzyme, wherein the lignocellulosic biomass is liquefied in the presence of a second endoglucanase enzyme prior to said fermenting, and wherein the production of said first endoglucanase enzyme is enhanced.

2. The method of claim 1, wherein the microorganism is *Aspergillus niger*.

\* \* \* \* \*